(12) United States Patent
Butikofer et al.

(10) Patent No.: US 6,677,749 B2
(45) Date of Patent: Jan. 13, 2004

(54) USING VARIABLE INDUCTANCE TO INDICATE ROLLER WEAR

(75) Inventors: Chet M. Butikofer, Meridian, ID (US); Robert W. Jewell, Meridian, ID (US); Ronald D. Edwards, Boise, ID (US)

(73) Assignee: Hewlett-Packard Development Company, L.P., Houston, TX (US)

( * ) Notice: Subject to any disclaimer, the term of this patent is extended or adjusted under 35 U.S.C. 154(b) by 93 days.

(21) Appl. No.: 10/121,146

(22) Filed: Apr. 10, 2002

(65) Prior Publication Data

US 2003/0193330 A1 Oct. 16, 2003

(51) Int. Cl.⁷ .............................................. G01N 27/72
(52) U.S. Cl. ...................................... 324/226; 324/239
(58) Field of Search .................................. 324/239, 240, 324/229, 207.17, 207.26, 226

(56) References Cited

U.S. PATENT DOCUMENTS

| | | | |
|---|---|---|---|
| 3,850,015 A | * 11/1974 | Andresen ..................... 324/229 |
| 3,902,114 A | * 8/1975 | Alich ......................... 324/229 |
| 4,210,403 A | 7/1980 | Mazouet et al. .......... 400/196.1 |
| 4,272,202 A | 6/1981 | Schroeder et al. ........... 400/208 |
| 4,297,045 A | 10/1981 | Burton et al. ................ 400/641 |
| 4,448,559 A | 5/1984 | Matsuda et al. .......... 400/637.4 |
| 4,502,804 A | 3/1985 | Willcox ....................... 400/641 |
| 4,548,523 A | 10/1985 | McGourty et al. ........... 400/617 |
| 5,092,695 A | 3/1992 | Silverman et al. ........... 400/249 |
| 5,533,822 A | 7/1996 | Tsukada et al. ............. 400/641 |
| 5,660,489 A | 8/1997 | Ishii et al. .................. 400/641 |
| 5,850,233 A | 12/1998 | Otsuka et al. ............... 346/136 |
| 6,055,047 A | 4/2000 | Schweizer et al. ........ 356/237.1 |

* cited by examiner

*Primary Examiner*—Walter E. Snow
(74) *Attorney, Agent, or Firm*—James R. McDaniel

(57) ABSTRACT

This invention relates to the method and apparatus for indicating roller wear in a media handling device. Such structures of this type, generally, employ the use of variable inductance to determine roller wear. The media transport roller has a non-conductive surface with a conductive core. Located just above the conductive core is a rod containing a power coil that is driven by AC excitation and a pick-up coil. The pick-up coil is connected to circuitry that measures the inductance. As the media transport roller wears, the conductive core moves closer to an inductive pick-up unit. The measured output voltage from the pick-up unit depends upon the distance between the core and the pick-up unit. This inductance change can then be correlated to media transport roller wear and relayed to the user through the use of an LED or other similar types of numerical/graphical displays.

12 Claims, 2 Drawing Sheets

USING VARIABLE INDUCTANCE TO INDICATE ROLLER WEAR

FIELD OF THE INVENTION

This invention relates to the method and apparatus for indicating roller wear in a media handling device. Such structures of this type, generally, employ the use of variable inductance to determine roller wear. The media transport roller has a non-conductive surface with a conductive core. Located just above the conductive core is a rod containing a power coil that is driven by AC excitation and a pick-up coil. The pick-up coil is connected to circuitry that measures the inductance. As the media transport roller wears, the conductive core moves closer to an inductive pick-up unit. The measured output voltage from the pick-up unit depends upon the distance between the core and the pick-up unit. This inductance change can then be correlated to media transport roller wear and relayed to the user through the use of an LED or other similar types of graphical/numerical displays.

DESCRIPTION OF THE RELATED ART

Prior to the present invention, as set forth in general terms above and more specifically below, it is known, in the media handling device art, to make use of a device for determining roller wear. Exemplary of such prior art is U.S. Pat. No. 6,055,047 ('047) to A. Schweizer et al., entitled "Device for Determining the Degree of Wear of a Paper Transport Roller." The '047 reference discloses a paper transport roller which comprises two layers having different degrees of reflection for electromagnetic radiation. When the outer layer is worn, the degree of reflection of the surface of the paper transport roller changes and the user is signaled that paper transport roller must be replaced. However, if a foreign object becomes attached to the transport roller of the '047 reference, this foreign object could adversely affect the reflection characteristics of the device. Also, if the paper transport roller does not wear evenly, one edge of the roller may have a different degree of reflection than the other edge of the roller and, possibly, adversely affect the reflection characteristics of the device. Therefore, a more advantageous paper transport roller wear indication system, then, would be presented if the system did not have to rely on a paper transport roller which comprises two layers having different degrees of reflection.

It is apparent from the above that there exists a need in the art for a paper transport roller wear indication system which is lightweight through simplicity of parts and uniqueness of structure, and which these equals the wear indication characteristics of the known paper transport roller wear indication systems, but which at the same time employs variable inductance which will alert the user to the worn condition of the paper transport roller. It is a purpose of this invention to fulfill this and other needs in the art in a manner more apparent to the skilled artisan once given the following disclosure.

SUMMARY OF THE INVENTION

Generally speaking, this invention fulfills these needs by providing a method for indicating media transport roller wear, wherein the method is comprised of steps of: creating a variable inductance between a pick-up unit located substantially adjacent to a media transport roller and a conductive surface located on the roller; and indicating an amount of roller wear by measuring a change in the variable inductance.

In certain preferred embodiments, the pick-up unit consists of a power coil that is driven by AC excitation and a pick-up coil. Also, the media transport roller conductive surface is a conductive core upon which the media transport roller rotates. Finally, the method further includes step of tracking the rotations of the media transport roller such that the power coil would not need to be activated until the media transport roller had completed a predetermined number of rotations.

In another further preferred embodiment, the wear of the media transport roller can be accurately detected so that the user can be alerted that the roller needs to be replaced and/or serviced.

The preferred media transport roller wear indicating system, according to this invention, offers the following advantages: lightness in weight; ease of assembly and repair; excellent roller wear indicating characteristics; good stability; good durability; and excellent economy. In fact, in many of the preferred embodiments, these factors of lightness in weight, ease of assembly and repair, excellent roller wear indicating characteristics, and excellent economy are optimized to an extent that is considerably higher than heretofore achieved in prior, known media transport roller wear indicating systems.

The above and other features of the present invention, which will become more apparent as the description proceeds, are best understood by considering the following detailed description in conjunction with the accompanying drawing figures, wherein like characters represent like parts throughout the several views and in which:

DETAILED DESCRIPTION OF THE INVENTION

Figure 1:
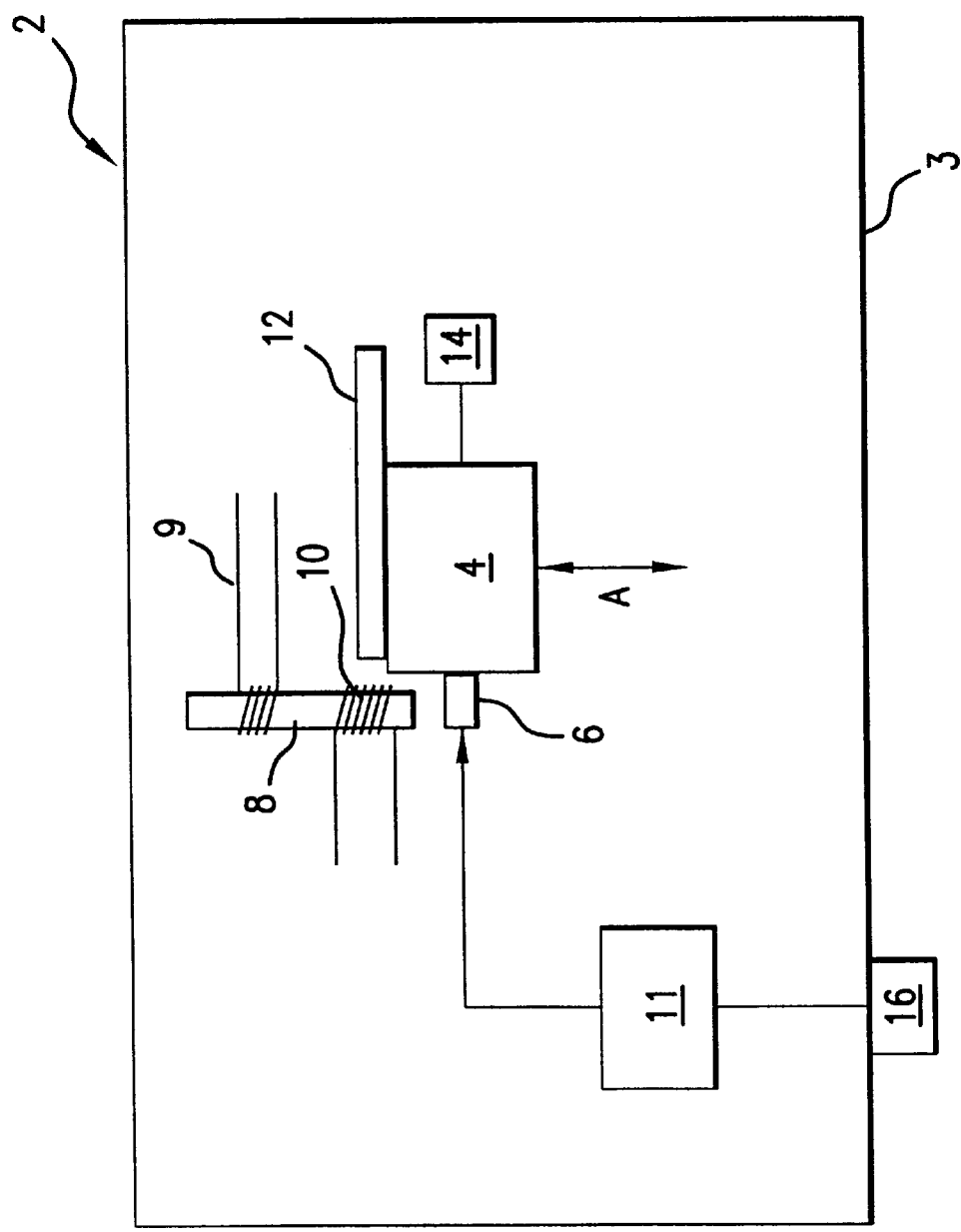
FIG. 1 is a schematic illustration of a media transport roller wear indicating system, according to one embodiment of the present invention.

With reference to FIG. 1, there is illustrated one preferred embodiment for use of the concepts of this invention. Media transport roller wear indicating system 2 for indicating media transport roller wear is illustrated in FIG. 1. System 2 includes, in part, media handling device 3, conventional media transport roller 4, conductive core 6, conventional pick-up unit rod 8, conventional pick-up unit power coil 9, conventional pick-up unit pick-up coil 10, conventional variable inductance measurement means 11, conventional hard stop 12, conventional media transport roller rotation counting means 14, and media transport roller wear indicating/display means 16. It is to be understood that a conventional pick-up unit consists of rod 8, pick-up unit power coil 9, and pick-up coil 10.

Media handling device 3 can be, but is not limited to, a paper handler, a printer, a copier, a facsimile machine, a printing device or the like. It is to be understood that media transport roller 4, preferably, is a conventional pick-up media transport roller that moves up and down along the directions of arrow A. Conductive core 6 is, preferably, constructed of any suitable, durable, conductive material that is capable of conducting electricity. It is being understood that any suitable, durable, non-conductive material, such as rubber, can be used in media transport roller 4 to conventionally encircle conductive core 6. Hard stop 12, preferably, is constructed of any suitable, durable, non-conductive material, such as a polymeric material, that does not adversely affect the wear characteristics of media transport roller 4.

is to be understood that hard stop 12 provides a reference point to determine a change in variable inductance. What is meant by this is that media transport roller 4 initially contacts hard stop 12. The initial distance between conductive core 6 and pick-up coil 10 can be measured to provide an initial/reference variable inductance.

Media transport roller rotation counting means 14, preferably, is any suitable, durable device that is capable counting the number of rotations of media transport roller 4. It is to be understood that media transport roller wear indicating/display means 16 must adequately notify the user of the state of wear of media transport roller 4. For example, media transport roller wear indicating/display means 16 can be a LED that changes colors based upon the amount of wear of media transport roller 4. Also, media transport roller wear indicating/display means 16 could also include a visual display means (not shown) that provides a visual text to the user regarding the wear status of media transport roller 4.

During the operation of system 2, media transport roller 4 moves up and down along the directions of arrow A. Hard stop 12 is used to limit the upward movement of media transport roller 4. As media transport roller 4 is rotating and moving up and down, power coil 9 is conventionally driven by an AC excitation. This AC excitation is converted into a magnetic flux that travels through rod 8 to pick-up coil 10, which supplies the output voltage. As media transport roller 4 moves up and down along the directions of arrow A, the distance between conductive core 6 and pick-up coil 10 varies. This variable distance causes a change in output voltage between conductive core 6 and pick-up coil 10 and creates a variable inductance that is conventionally measured by variable inductance measurement means 11. As media transport roller 4 wears down, conductive core 6, on average, gets closer to pick-up coil 10.

As discussed above, the measured output voltage depends upon the distance between pick-up coil 10 and conductive core 6. This inductance change can then be conventionally correlated to the wear of media transport roller 4 in a lookup table and/or an algorithm and related to the user through transport roller wear indicating/display means 16. For example, as long as media transport roller 4 is not sufficiently worn down, the user can be assured through media transport roller wear indicating/display means 16, such as the showing of a "green" light in transport roller wear indicating/display means 16, that media transport roller 4 is not adversely worn.

Once media transport roller 4 has been sufficiently worn down, the user can be assured through media transport roller wear indicating/display means 16, such as showing of a "red" light in media roller wear indicating/display means 16, that media transport roller 4 may be suffering from adverse wear and media transport roller 4 may need to be replaced or serviced. It is also to be understood that a visual display (not shown) on media roller wear indicating/display means 16 can also provide the user with up-to-date numerical/graphical information regarding the amount of wear of media transport roller 4.

In another embodiment of the present invention, media transport roller rotation counting means 14 can be used to conventionally count the number of rotations of media transport roller 4. In this manner, power coil 9 would not have to be activated until a predetermined number of rotations of media transport roller 4 have been achieved. This eliminates the need to continuously utilize power coil 9, pick-up coil 10, and variable inductance measurement means 11 until needed in system 2.

Figure 2:
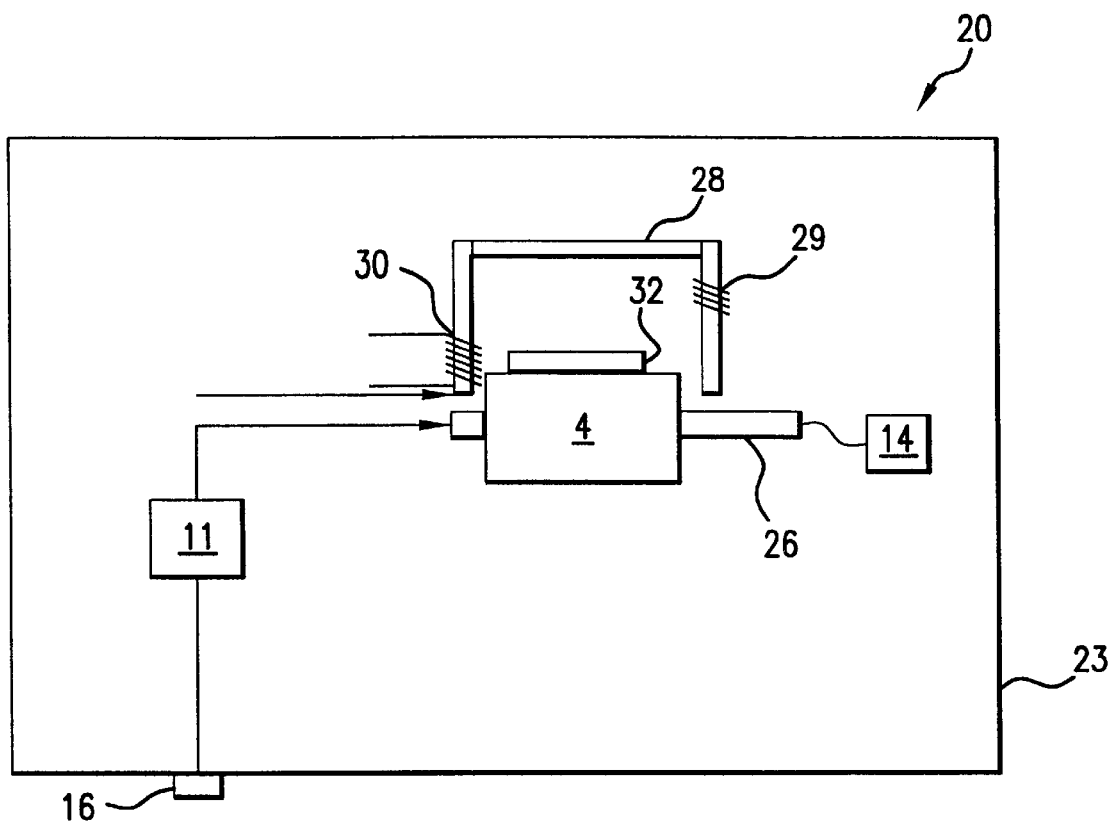
FIG. 2 is a schematic illustration of a media transport roller wear indicating system, according another embodiment of the present.
Figure 3:
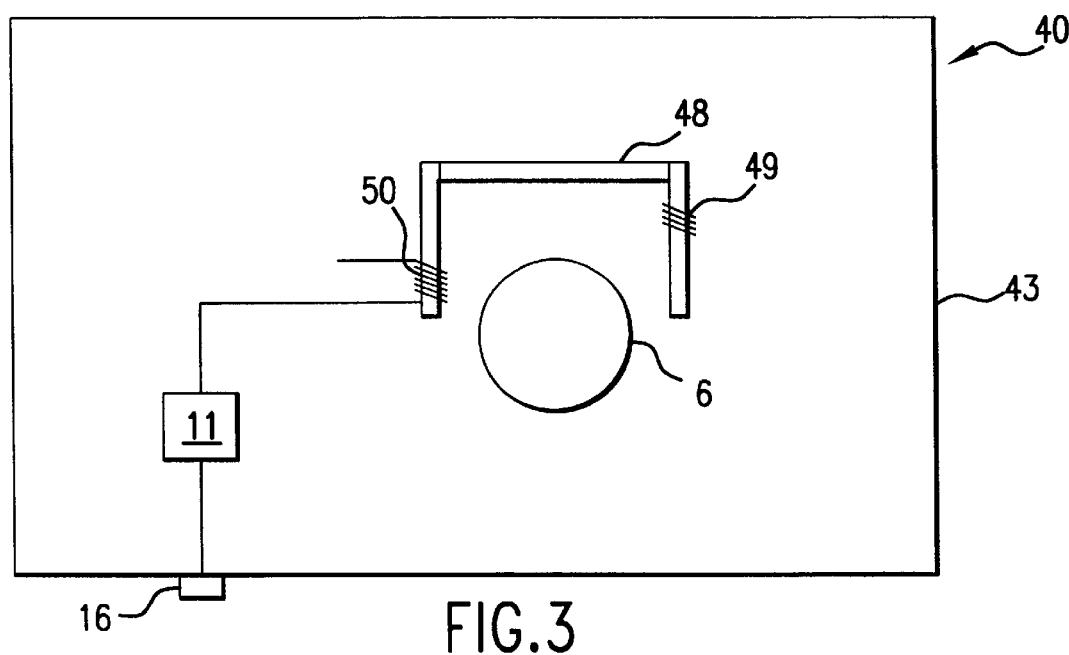
FIG. 3 is a side view, schematic illustration of a media transport roller wear indicating system, according to still another embodiment of the present invention.

In still another embodiment of the present invention, media transport roller wear indicating system 20 is illustrated. As shown in FIG. 2, system 20 includes, in part, media handling device 23, conductive core 26, U-shaped rod 28 that is connected to power coil 29 and pick-up coil 30, and hard stop 32. As discussed above, rod 28, power coil 29 and pick-up coil 30 make up the pick-up unit for system 20. As can be seen, conductive core 26 extends across both ends of the pick-up unit and core 26 is constructed of the same materials as core 6 (FIG. 1). It is to be understood that rod 28, power coil 29, pick-up coil 30, and hard stop 32 are constructed in the same manner as rod 8, power coil 9, pick-up coil 10, and hard stop 12, respectfully (FIG. 1).

Finally, in a further embodiment of the present invention, media transport roller wear indicating system 40 is illustrated. System 40 includes, in part, media handling device 43, U-shaped rod 48 that is connected to power coil 49 and pick-up coil 50, and hard stop 52. As discussed above, rod 48, power coil 49, and pick-up coil 50 make up the pick-up unit for system 40. In this manner, conductive core 6 is located between the ends of the pick-up unit. It is to be understood that rod 48, power coil 49, pick-up coil 50, and hard stop 52 are constructed in the same manner as rod 8, power coil 9, pick-up coil 10, and hard stop 12, respectfully (FIG. 1).

Once given the above disclosure, many other features, modifications or improvements will become apparent to the skilled artisan. Such features, modifications or improvements are, therefore, considered to be a part of this invention, the scope of which is to be determined by the following claims.

What is claimed is:

1. A method for indicating media transport roller wear, comprising the steps of:

creating a variable inductance between a pick-up unit located substantially adjacent to a media transport roller and a conductive surface located on the roller;

indicating an amount of roller wear by measuring a change in the variable inductance; and counting a number of rotations of said media transport roller.

2. The method, as in claim 1, wherein said variable inductance creating step is further comprised of the step of:

creating an output voltage between said pick-up unit and said conductive surface.

3. The method, as in claim 2 wherein said creating an output voltage step is further comprised of the step of:

exciting a power coil of said pick-up unit.

4. The method, as in claim 1, wherein said counting step is further comprised of the step of:

activating said pick-up unit when a predetermined number of rotations of said media transport roller have been achieved.

5. The method, as in claim 1, wherein said indicating step is further comprised of the step of:

operating a light means to indicate a wear status of said media transport roller.

6. The method, as in claim 1, wherein said indicating step is further comprised of the step of:

displaying an amount of wear of said media transport roller.

7. A system for indicating media transport roller wear, comprising:

a media transport roller having a conductive surface;

a pick-up unit located adjacent to said conductive surface;

a media transport roller wear indicating means operatively connected to said conductive surface and said pick-up unit; and a media transport roller rotation counting means operatively connected to said media transport roller.

8. The system, as in claim 7, wherein said pick-up unit is further comprised of:

a rod means;

a power coil means operatively connected to one end of said rod means; and a pick-up coil means operatively connected to another end of said rod means.

9. The system, as in claim 7, wherein said media transport roller wear indicating means is further comprised of:

a variable inductance measurement means operatively connected to said conductive surface and said pick-up unit; and a display means operatively connected to said variable inductance measurement means.

10. The system, as in claim 9, wherein said display means is further comprised of:

a light means.

11. The system, as in claim 10, wherein said light means is further comprised of:

a light means that changes colors based upon a wear status of said media transport roller.

12. The system, as in claim 9, wherein said display means is further comprised of:

a graphical/numerical visual display.

* * * * *